(12) United States Patent
Dolak

(10) Patent No.: US 6,803,056 B2
(45) Date of Patent: Oct. 12, 2004

(54) METHOD AND COMPOSITION FOR TREATING VIRAL OUTBREAKS

(76) Inventor: Terence M. Dolak, 27 Mountain View Dr., Andover, NJ (US) 07821

(*) Notice: Subject to any disclaimer, the term of this patent is extended or adjusted under 35 U.S.C. 154(b) by 0 days.

(21) Appl. No.: 10/385,099

(22) Filed: Mar. 10, 2003

(65) Prior Publication Data
US 2003/0152640 A1 Aug. 14, 2003

Related U.S. Application Data

(63) Continuation-in-part of application No. 10/151,347, filed on May 20, 2002, now abandoned, which is a continuation-in-part of application No. 09/952,119, filed on Sep. 14, 2001, now abandoned.

(51) Int. Cl.$^7$ ............................................... A61K 35/64
(52) U.S. Cl. ....................................... 424/539; 424/520
(58) Field of Search .................................. 424/539, 520

(56) References Cited

U.S. PATENT DOCUMENTS

| | | |
|---|---|---|
| 4,699,791 A | 10/1987 | Tabord |
| 4,748,022 A | 5/1988 | Busciglio |
| 5,449,794 A | 9/1995 | Markonius |
| 5,591,771 A | 1/1997 | Markonius |
| 5,861,430 A | 1/1999 | Markonius |
| 5,977,176 A | 11/1999 | Wise et al. |
| 6,027,716 A | 2/2000 | Levin et al. |

OTHER PUBLICATIONS

Szmeja et al., *Otolaryng. Pol., XLI* (3) pp. 183–188 (1987).
Giurcaneanu et al., *Virologie,* 39(1), pp. 21–24 (1988).
Vynograd et al., *Phytomedicine* 7(1) pp. 1–6 (2000).
Villanueva et al., *Annals Inst. Pasteur Paris* 118(1), pp. 84–87 (1970).
Schneiderweind et al., *Pharmazie,* 30(12), p. 603 (1975).
Park et al., *Biosci. Biotechnol. Biochem.,* 62(11) pp. 2230–2232 (1988).
Markham et al., *Phytochemistry* 42(1), pp. 205–212 (1996).
Pepeljnjak et al., *Pharmazie* 40(2) pp. 122–123 (1985).

*Primary Examiner*—Leon B. Lankford, Jr.
(74) *Attorney, Agent, or Firm*—Gibbons, Del Deo, Dolan, Griffinger and Vecchione

(57) ABSTRACT

The invention provides a method and composition for treatment of lesions associated with viral infections, such as human Herpes simplex, by applying to the lesions an effective amount of a topical composition comprising: propolis extract in from about 0.5 to 10%, preferably about 1 to 8%, by weight; a skin protectant in from about 0.5% to 50% by weight; a penetration enhancing agent in from about 5 to 30%, preferably 5 to 25%, by weight; and an emulsifier in from about 1 to 20% by weight. The subject compositions possess enhanced activity in the treatment of such lesions in that they stop the outbreak at the stage of progression when they are applied and promote full healing, generally within 36 to 48 hours.

9 Claims, No Drawings

METHOD AND COMPOSITION FOR TREATING VIRAL OUTBREAKS

RELATED APPLICATIONS

This application is a continuation-in-part of U.S. patent application Ser. No. 10/151,347, filed May 20, 2002, now abandoned, which in turn is a continuation-in-part of U.S. patent application Ser. No. 09/952,119, filed Sep. 14, 2001, now abandoned.

FIELD OF THE INVENTION

This invention relates to a method and composition for the treatment of lesions associated with viral infections, such as Herpes simplex or Herpes zoster.

BACKGROUND OF THE INVENTION

Herpes viral infections are chronic. Once the virus enters the body, it lies dormant in the nerve cells and periodically reactivates. When the virus reactivates, it characteristically causes a sore at the site where it first entered the body. To date, there is neither a vaccine to prevent the Herpes infection, nor any way to eliminate the virus from the body. Once infected, the patient has the virus for life.

Recurrent outbreaks of the Herpes virus generally follow a staged progression. The stages are easily identifiable and include prodrome, vesicles, ulceration, crust and healing. Some of these stages can last less than 24 hours. Prodrome is generally a short period of tingling, itching, numbness or burning with no visible sign of an outbreak. Vesicles is the formation of one or more fluid-filled blisters, often in a cluster and usually surrounded by sore, red skin. The ulceration stage is when the blisters open to form painful ulcers or open sores. At the edge of the sore, a soft or hard yellow crust begins to appear. Ulcers and painful, sore, red skin persist through this stage. At the crust stage, weeping sores or ulcers become completely covered by a crust or scab. No ulcers or blisters are present. The healing process is manifested by disappearance of the crust, swelling, pain and itching. Skin eruptions due to viral infection, especially Herpes viruses, generally have a normal infective course that lasts from 10 to 60 days depending on the exact causative species and anatomical location of the infection.

Propolis has been used in both water-based and oil-based preparations to treat viral outbreaks. Propolis preparations are reported to reduce the healing process by up to 50% or from an average of 9 to 10 days to an average of 4 to 5 days. In a placebo-controlled study involving 50 patients with recurrent oral Herpes, a commercial petroleum-based propolis ointment (Herpestat or HelaStop) reduced healing time by 50%, Szmeja and Konopacki, *Otolaryng. Pol.,* XLI(3): 183–188 (1987). The average healing time for the placebo patients was 8 days and the average healing time for patients using Herpestat, which is also called Herstat, was 4 days. The same results were reported for a placebo controlled study using a commercial aqueous propolis extract solution, Nivcrisol-D Giurcaneanu et al., *Virologie,* 39(1):21–24 (1988). This study involved 65 patients. Patients using placebo had an average healing time of 8 days and those using Nivcrisol-D, an average healing time of 4 days.

In a placebo controlled study involving 90 patients with recurrent genital Herpes, the efficacy of acyclovir ointment and a petrolatum based propolis ointment (HelaStop) were compared. The average healing time for both the placebo and acyclovir ointment was 12 days and an average healing time for the propolis ointment group was 8–9 days, Vynograd et al., *Phytomedicine,* 7(1):1–6 (2000). In Table 3 of Vynograd eta, it is reported that of 30 patients treated with a propolis preparation, none had healed Herpes lesions after three days, only 10 had healed after seven days and 24 had healed after ten days.

Busciglio, U.S. Pat. No. 4,748,022 discloses compositions comprising diphenhydramine HCl, lidocaine HCl, aloe vera gel and propolis in a formulation having a basic pH. In the comparative data, while the composition containing all ingredients was superior to a similar formulation without the aloe vera gel and propolis, a formulation omitting only propolis demonstrated about 40% better average healing time than the formulation containing all ingredients. It should be noted that one subject reported no healing with the formulation omitting propolis. Regardless, the results must be viewed as inconclusive in terms of the capacity of the formulation ingredients to enhance the efficacy of propolis.

It is evident from these results that there is still a need for an effective treatment. It has been found that by using propolis in the compositions of the present invention, the healing time of Herpes outbreak is dramatically reduced to 36–48 hours and material progression of the outbreak is prevented beyond the stage of progression at the time of the initial application.

SUMMARY OF THE INVENTION

The present invention relates to topical preparations and methods for treatment of skin and mucosal membrane lesions associated with viral infections, such as Herpes simplex or Herpes zoster. More specifically, the present invention provides a composition and method for the treatment of lesions associated with Herpes viruses that reduces the healing time of a Herpes outbreak and stops the outbreak on contact with full healing, generally in 36 to 48 hours.

In particular, the present invention provides a composition for the treatment of lesions associated with viral infections comprising: propolis extract, a skin protectant, a penetration enhancing agent and an emulsion base. The present invention also provides a method for the treatment of lesions associated with viral infections comprising applying to the lesion an effective amount of the subject compositions.

DETAILED DESCRIPTION OF THE INVENTION

The present invention provides topical compositions and method for the treatment of lesions associated with viral infections, such as Herpes viruses. In the foregoing discussion, the progression of a viral outbreak was given as: prodrome, vesicles, ulceration, crust and healing. For brevity, the term "lesion" as utilized herein shall refer to any and all of such stages. Those of ordinary skill in the art will recognize that a lesion in this context designates any occurrence in the progression other than normal skin. Intraorally, lesions will manifest themselves as ulcers on the hard palate and dorsal tongue only. Intraoral lesions are not to be confused with idiopathic aphthous ulcers that occur on the movable oral mucosal. Idiopathic aphthous ulcer lesions are sufficiently distinctive in appearance to differentiate them from primary or recurrent herpetic oral lesions. In accordance with the present invention, application of the subject compositions not only dramatically reduces the healing time of Herpes lesions, but also stops the normal progression of the Herpes outbreak from the stage at which the initial application occurred. On the average, the present compositions reduce healing time of a Herpes outbreak to 36 to 48 hours.

The compositions of the present invention are those recognized in the pharmaceutical arts as being suitable for topical application and include, without intended limitation, creams, lotions, liquid emulsions and the like. The present compositions comprise: propolis extract in from about 0.5 to 10%, preferably from about 1 to 8%, by weight; a skin protectant in from about 0.5 to 50% by weight; a penetration enhancing agent in from about 1 to 30%, preferably 5 to 25%, by weight; and an emulsifier in from about 1 to 20% by weight. The careful selection of each of the components of the present compositions has provided an optimal antiviral effect that has produced unexpectedly enhanced results. In addition to the surprising enhanced therapeutic effect, the subject compositions are advantageous in that the skin protectant protects against the irritation and resultant bacterial infections that tend to exacerbate a viral outbreak.

The skin protectant forms a barrier over the skin surface to help protect against irritation due to touching, itching, topical care products, chafing, etc. In the treatment of Herpes lesions on mucosal membranes, e.g. the oral cavity, the skin protectant, in addition to forming a protective barrier, provides a hydrophobic environment at the site of application that aids in preventing loss of the active ingredient to the action of saliva. The skin protectant comprises at least one member selected from the group consisting of allantoin, aluminum hydroxide gel, dimethicone, glycerin, kaolin, pyridoxine hydrochloride, topical starch, petrolatum, and white petrolatum. Preferred skin protectants, with their preferred concentrations in percent by weight, include one or more members selected from the group consisting of dimethicone 0.5–5.0%, allantoin 0.5–5.0%, glycerin 1.0–8.0%, petrolatum 5–50%, and white petrolatum 5–50%. For treatment of lesions on the oral mucosal membranes, aluminum hydroxide gel 5–20%, kaolin 2–10% and topical starch 1–15% are preferred for forming a physical barrier and dimethicone 0.5–5.0%, petrolatum 5–50% and white petrolatum 5–50% are preferred for providing a hydrophobic environment at the site of application.

The compositions of the present invention contain a penetration enhancing agent that helps facilitate the delivery of the active principle of propolis through the cornified layer of the skin to the layers of the skin where the viral infection and replication processes are ongoing. The penetration enhancing agent comprises ethanol or a combination thereof with at least one member selected from the group consisting of glycerol esters, propylene glycol, butylene glycol, cyclic amides, 1-dodecyl-aza-cyclophetan-2-one, 2-pyrrolidone, diisopropyl sebacate, $C_{1-30}$ alkyl esters of pyroglutamic acid, 1-methyl-2-pyrrolidone, 2-hydroxyoctanoic acid, polyoxylene sorbitan mono-oleates, polysorbate 80, polysorbate 60, fatty alcohols, alkylene glycol esters, diethylene glycol, diethylene glycol monoethyl ether, diethylene glycol monomethyl ether, dipropylene glycol and art recognized derivatives thereof possessing a like activity. Wherein ethanol is present in the compositions of the invention in combination with one of the other agents listed above, it is preferred that the concentration of ethanol does not exceed about 10% by weight, based on the overall composition. Ethanol is present in the compositions of the invention in propolis extract which is typically a 50% tincture in ethanol. Preferred penetration agents in accordance with the present invention are ethanol in combination with propylene glycol or polysorbate 60.

The emulsifier of the present composition provides a means of achieving a molecular dispersion of the active principals in propolis extract, the majority of which have limited water solubility. The poor solubility impedes the penetration of the active principals, particularly the flavonoid components, into the skin and, therefore, their ability to reach the viral infection site. The emulsifier also aids in hydrating the surface of the skin at the site of application, thereby further improving propolis absorption.

The emulsifier comprises at least one member selected from the group consisting of sorbitan derivatives, particularly sorbitan esters with fatty acids such as oleic acid, alkoxylated alcohols, polymeric ethers, glycerol esters, poly (oxyethylene-oxypropylene)-methylpolysiloxane copolyiners and their derivatives and water soluble salts of fatty acids with ammonia, alkanolamines, low molecular weight amines and alkali metals, such as sodium and potassium. It is within the purview of the present invention that certain of the emulsifiers listed above can function as penetration enhancing agents as well. Preferred emulsifiers include one or more of polysorbate 60, polysorbate 80, a polyethylene glycol and a sorbitan ester.

In addition to the foregoing essential ingredients, the compositions of the present invention may contain other ingredients such as are recognized by those skilled in the pharmaceutical compounding arts as being typically present in such formulations. These include, without intended limitation, one or more preservatives, osmotic regulators, thickeners, flavors, fragrances, emollients, humectants, colorants, pigments and the like. It will be appreciated that the compounding of the compositions of the present invention will be carried out utilizing some or all of these ingredients depending of the intended use. For example, for a lotion, colorants or pigments as well as humectants may be present and for a preparation intended for application in or around the mouth, it will be necessary to add flavors to mask the taste of the essential ingredients, particularly the propolis extract.

In addition to the choice of these additional ingredients, the intended use of the composition will influence the choice of certain of the essential ingredients as well, e.g. ingredients that are liquid or semisolid will be utilized to prepare a lotion and those of a higher molecular weight will be used to prepare ointments and the like. The choice of such ingredients is considered to be within the purview of the person skilled in the art of pharmaceutical compounding for a given type of preparation. The present compositions are preferably formulated to be hypoallergenic and are packaged in an antiseptic condition to minimize the possibility of complicating infections.

It has been found in accordance with the present invention, that application of the subject compositions at the prodrome stage, of a Herpes outbreak before vesicle formation, will preclude the formation of a visible sore or inflammation. Therefore, the present invention provides a method for treatment of lesions associated with viral infections comprising applying to the lesion an effective amount of the subject compositions. The method of this invention is particularly effective, where the viral infection is Herpes simplex or Herpes zoster.

The present invention is further illustrated by the following examples that are not intended in any way to be limiting thereon.

EXAMPLE 1

A cream containing 4% by weight of propolis extract was prepared from formula 1 given below.

| Formula 1 | | | |
|---|---|---|---|
| Ingredient | Quantity | Ingredient | Quantity |
| Propolis Extract | 4 g | Cetyl Alcohol | 2 g |
| Ethanol | 4 g | Glyceryl Stearate | 1 g |
| Dimethicone | 2 g | Propylene Glycol | 5 g |
| Stearic Acid | 7 g | Tocopherol Acetate | 0.2 g |
| Polysorbate 80 | 3 g | Methyl Paraben | 0.3 g |
| PEG-100 Stearate | 1 g | Propyl Paraben | 0.1 g |
| Beeswax | 0.5 g | Triethanolamine | 1 g |
| Carbomer | 0.5 g | Disodium EDTA | 0.1 g |
| Hydrogenated Polyisobutene | 3 g | Water | q.s. 100 g |

The dimethicone, PEG-100 stearate, beeswax, hydrogenated polyisobutene, cetyl alcohol, glyceryl stearate, tocopherol acetate, methyl and propyl paraben were combined in a suitable vessel with heating to 70–80° C. The resulting anhydrous mixture was held at 70–80° C. with continuous mixing until uniform.

In a second vessel, stearic acid, carbomer, triethanolamine, disodium EDTA and 60 mL of water were combined and gradually heated to 70–80° C. until the resulting aqueous mixture became uniform. The aqueous mixture was slowly added to the anhydrous mixture at 70–80° C. with very rapid mixing. The resulting mixture was homogenized to form an emulsion that was subsequently cooled to 40–50° C.

The propolis extract was placed in a third vessel with ethanol and propylene glycol gradually added thereto with stirring, followed by the polysorbate 80. The temperature was gradually increased to 40° C. with continuous mixing. When the mixture became uniform, it was slowly added to the homogenized emulsion with rapid stirring. The emulsion was then brought to final weight by the slow addition of the required amount of water with continued blending. The emulsion was again homogenized and cooled to a smooth, creamy consistency.

EXAMPLE 2
Treatment of Herpes Simplex Patients with the Composition

The cream prepared in Example I was tested for its effectiveness against the Herpes virus. In order to compare the effectiveness of the composition in preventing Herpes outbreak, four case studies were observed.

Case I
History of Herpes Infection

A 47 year old male with a history of fever blisters since the age of 11 and an average of 18 outbreaks per year, had tried treating the infections with oral prescription (Valtrex®), inoculations, topical over-the-counter (OTC) drugs, folic acid, acyclovir, herbal remedies, topical pain relievers and antibiotics, all with no success.

The patient's symptoms included the prodromal phase of itching, heat and pain of the affected area. His blisters ranged from small singular blisters to large multi-blister formations with a size range from 1 mm to covering the entire oral area from below the nose to the chin. This usually necessitated the treatment with steam to open the mouth after the blisters ruptured. The blisters typically lasted for 8–12 days or longer for multi-blister formations or when infections were involved.

Composition Treatment and Results

First Outbreak: The patient awakened at 1:30 a.m. with a burning itching area on the upper left quarter of his lips. He liberally applied the composition to the infected area and obtained immediate relief. The composition was reapplied at 5:30 a.m. and 9:30 a.m. The entire area was normal by 11:30 a.m. No further applications were made and no blisters formed.

Second outbreak: Upon awakening at approximately 6:00 a.m., the patient observed that a 4-mm blister had already formed. He applied the composition every 2–3 hours for the first day. The pain, itching and burning were effectively eliminated. On the second and third days, the composition was applied three times a day, in the morning, at noon and before bedtime. The blisters did not rupture and were reabsorbed. No infections or redness occurred. By the end of the third day, there was no longer any visible evidence of the blisters.

Current Status

For the past nine months, the patient has been applying the composition each night before bedtime. During this period, he has experienced only two outbreaks, both of which resulted from his traveling without the composition. In each instance, prompt application of the composition, resolved the outbreak and eliminated all infections and redness within 48 hours or less.

Case II
History of Herpes Infection

A 44 year old female with a history of fever blisters since her early teen years and an average of six outbreaks per year had tried oral prescription (Valtrex®) inoculations, topical over-the-counter (OTC.) drugs, folic acid, acyclovir, topical pain relievers and antibiotics for infections, all without success. Her symptoms included prodromal phase of itching, heat and pain. Her blisters ranged from small singular blisters to large multi-blister formation with a variation in size from 1 mm to covering the entire oral area from below the nose to the chin.

Composition Treatment and Results

At the first sign of an outbreak, the patient applied the composition as soon as possible upon returning home at night, once before bed and again in the morning. The composition was not applied during the day. She reported that application of the composition during the prodromal stage prevented blistering on three occasions. On two other occasions, she was not able to apply the composition until blisters had already formed. In both occasions, she maintained the same application schedule and reported remission of the blisters within 2 days, with a substantial reduction in pain and no redness or infection.

Case III
History of Herpes Infection

A 34 year old female with a history of occasional cold sores approximately one every two months. Her symptoms included prodromal phase of itching and sharp burning pain that centered on the cold sore and the development of infection. Her blisters ranged from 1 mm to 5 mm and typically remained for 10–12 days.

Composition Treatment and Results

At the first sign of an outbreak, the patient applied the composition in the morning, before retiring to bed and again the following morning. She reported that all symptoms of the cold sore were gone by the evening of the second day. The composition was reapplied again on the second day before retiring to bed. By the third day, no further symptoms were visible and no vesicles, blisters or ulcers ever formed. The patient experienced complete resolution in less than 48 hours from the initial application of the composition.

Case IV
History of Herpes Infection

A 37 year old female with a history of occasional cold sores approximately one every four months. Her symptoms included prodromal phase of itching, heat and pain. Her blisters ranged from small singular blisters to large multi-blister formation with varied sizes and typically remained for 10–12 days.

Composition Treatment and Results

The patient applied the composition after the formation of vesicles and continued with applications every 3–4 hours for the next two days. She indicated that she obtained almost immediate relief from the pain and felt little or no discomfort during this time. All visible signs of the cold sores disappeared by the third day.

The foregoing case studies demonstrate the enhanced effectiveness of compositions in accordance with the present invention in the treatment of lesions caused by Herpes infections and idiopathic aphthous ulcers.

EXAMPLE 3

A cream containing 4% by weight of propolis extract was prepared from Formula 2 given below.

| Formula 2 | | | |
|---|---|---|---|
| Ingredient | Quantity | Ingredient | Quantity |
| Propolis Extract | 4 g | Cetyl Alcohol | 3 g |
| Ethanol | 4 g | Tocopherol Acetate | 0.2 g |
| Cyclomethicone | 4 g | Polyaminopropyl | 4 g |
| Polysorbate 60 | 6 g | Biguanide (20%) | |
| Dimethicone | 2 g | Water | q.s. 100 g |
| PEG-100 Stearate | 2 g | | |

The dimethicone, cyclomethicone, PEG-100 stearate, cetyl alcohol, and tocopherol acetate were combined in a suitable vessel with heating to 70–80° C. The resulting anhydrous mixture was held at 70–80° C. with continuous mixing until uniform.

The Propolis extract, ethanol, polysorbate 60 and polyaminopropyl biguanide solution were placed in a second vessel with 20 g of water with stirring. The temperature of the mixture was slowly raised to 40° C. with continuous mixing. When the mixture became uniform, it was slowly added to the anhydrous mixture with continuous, rapid stirring. The resulting emulsion was brought to final weight by the slow addition of the required amount of water with continuous blending. The emulsion was homogenized and cooled to a smooth, creamy consistency.

EXAMPLE 4
Treatment of Herpes simplex Patients with Variations of Formula 2

Patients participating in the study were instructed to apply the test preparation at the first sign of a cold sore lesion and to continue to apply it four to six times daily until the lesion was healed. The patients were instructed to note the time of each application and to indicate at each application the stage of the outbreak as well as the level of pain they were experiencing. They were also asked to measure the size of the lesion once daily. These entries were maintained in a diary that was utilized to determine mean time from onset to healing of the cold sores, outbreak progression and pain relief. Two patients received each of the formulations given below. The formulations were prepared in the manner given in the previous Examples. Formula 2 is representative of the formulations of the present invention. Formula 2d is a control formula containing no propolis and each of formulae 2a through 2c contains propolis, but omits another component as will be discussed. The results are given in the following Table.

| Ingredients | Formula 2 | Formula 2a | Formula 2b | Formula 2c | Formula 2d |
|---|---|---|---|---|---|
| Propolis Extract | 4.0 g | 4.0 g | 4.0 g | 4.0 g | — |
| Ethanol | 4.0 g | 4.0 g | 4.0 g | 4.0 g | 4.0 g |
| Dimethicone | 2.0 g | 2.0 g | — | 2.0 g | 2.0 g |
| Cyclomethicone | 4.0 g | 4.0 g | 4.0 g | — | 4.0 g |
| Cetyl Alcohol | 3.0 g | 3.0 g | 3.0 g | 3.0 g | 3.0 g |
| Polysorbate 60 | 6.0 g | — | 6.0 g | 6.0 g | 6.0 g |
| PEG-100 Stearate | 2.0 g | 2.0 g | 2.0 g | 2.0 g | 2.0 g |
| Tocopherol Acetate | 0.2 g | 0.2 g | 0.2 g | 0.2 g | 0.2 g |
| Polyaminopropyl Biguanide (20% solution) | 4.0 g | 4.0 g | 4.0 g | 4.0 g | 4.0 g |
| Water | qs 100 g | qs 100 g | qs 100 g | qs 100 g | qs 100 g |
| Average (n = 2) HSV-I healing time: | 1.9 days | 4.3 days | 4.6 days | 2.2 days | 8.4 days |

The results shown above demonstrate the special properties of the unique combination of components of the instant invention. The average healing time of oral Herpes simplex lesions with no treatment is 8 to 10 days. As shown by previous published studies, propolis can reduce the average healing time to 4.5–6 days, or by about 30–40%. This includes formulae containing skin protectants, such as petrolatum. The results obtained by the above variations of Formula 2 of the instant invention demonstrate a dramatic and unexpected reduction in the average healing time when propolis extract is used in combination with a skin protectant, an effective amount of an emulsifying agent and a penetration enhancing agent. With the component combination of the instant invention, average healing time is reduced to 1.9 days, or by 76–81%. As expected, the control formulation containing no propolis (formula 2d) produced an average healing time clinically equivalent to no treatment at all, i.e. about 8–10 days. The formulations containing propolis but without other essential ingredients of the subject compositions, i.e. the emulsifying agent (formula 2a) and the skin protectant (formula 2b), respectively, also resulted in a loss of efficacy compared to the complete composition of the instant invention.

Because propolis is present in the formulations as a 50% tincture, i.e. a solution in ethanol, it would not be possible to completely remove the penetration enhancing agent from the formulation. However, it can be seen that the omission of any of the other key formula components of the instant invention more than doubled the healing time from 1.9 days to 4–5 days. Formula 2c demonstrates that the removal of components other than the key components from the formulation produces very little change in the results obtained. In this instance, Cyclomethicone, an inorganic, silicone-based solvent is omitted from the formulation. It can be seen that the results are essentially comparable to the total formulation, i.e. an average healing time of 2.2 days. These results demonstrate the significant improvement realized with the formulations of the present invention.

What is claimed is:

1. A composition for topical treatment of skin and mucosal membrane lesions associated with viral infections comprising:
    (a) propolis extract in from about 1 to 8% by weight;
    (b) a skin protectant comprising one or more members selected from the group comprising of dimethicone, glycerin, petrolatum, and white petrolatum in from about 0.5 to 50% by weight;
    (c) a penetration enhancing agent selected from a combination of ethanol and propylene glycol or ethanol and polysorbate 60 in from 5 to 25% by weight; and
    (d) an emulsifier comprising one or more members selected from the group consisting of polysorbate 80, polysorbate 60 or other sorbitan ester in from 1 to 20% by weight.

2. A composition in accordance with claim 1, wherein the composition is a cream.

3. A composition in accordance with claim 1, wherein the composition is an emulsion.

4. A method for treatment of skin lesions associated with viral infections comprising applying to the lesion an effective amount of a composition comprising,
    (a) propolis extract in from about 1 to 8% by weight;
    (b) a skin protectant comprising one or more members selected from the group consisting of dimethicone, glycerin, petrolatum, and white petrolatum in from about 0.5 to 50% by weight;
    (c) a penetration enhancing agent selected from a combination of ethanol and propylene glycol or ethanol and polysorbate 60 in from 5 to 25% by weight; and
    (d) an emulsifier comprising one or more members selected from the group consisting of polysorbate 80, polysorbate 60 or other sorbitan ester in from 1 to 20% by weight.

5. A method in accordance with claim 4, wherein the lesions are caused by Herpes simplex.

6. A method in accordance with claim 4, wherein the lesions are caused by Herpes zoster.

7. A method in accordance with claim 4, wherein the composition is a cream.

8. A method in accordance with claim 4, wherein the composition is an emulsion.

9. A method for treatment of lesions of the oral mucosa associated with viral infections comprising applying to the lesion an effective amount of a composition comprising:
    (a) propolis extract in from about 1 to 8% by weight;
    (b) a skin protectant comprising one or more members selected from the group consisting of aluminum hydroxide gel, kaolin, topical starch, dimethicone, glycerin, petrolatum, and white petrolatum in from about 0.5 to 50% by weight;
    (c) a penetration enhancing agent selected from a combination of ethanol and propylene glycol or ethanol and polysorbate 60 in from 5 to 25% by weight; and
    (d) an emulsifier comprising one or more members selected from the group consisting of polysorbate 80, polysorbate 60 or other sorbitan ester in from 1 to 20% by weight.

* * * * *